United States Patent
Rizo et al.

(10) Patent No.: US 10,634,615 B2
(45) Date of Patent: Apr. 28, 2020

(54) METHOD OF CORRECTING A FLUORESCENCE IMAGE

(71) Applicants: Commissariat a l'energie atomique et aux energies alternatives, Paris (FR); FLUOPTICS, Grenoble (FR)

(72) Inventors: Philippe Rizo, La Tronche (FR); Anthony Daures, Grenoble (FR)

(73) Assignees: Commissariat a l'energie atomique et aux energies alternatives, Paris (FR); FLUOPTICS, Grenoble (FR)

( * ) Notice: Subject to any disclaimer, the term of this patent is extended or adjusted under 35 U.S.C. 154(b) by 0 days.

(21) Appl. No.: 15/573,339

(22) PCT Filed: May 11, 2016

(86) PCT No.: PCT/FR2016/051114
§ 371 (c)(1),
(2) Date: Nov. 10, 2017

(87) PCT Pub. No.: WO2016/181076
PCT Pub. Date: Nov. 17, 2016

(65) Prior Publication Data
US 2018/0136129 A1    May 17, 2018

(30) Foreign Application Priority Data
May 12, 2015 (FR) .................................. 15 54260

(51) Int. Cl.
*G01N 21/64* (2006.01)
*A61B 5/00* (2006.01)
(Continued)

(52) U.S. Cl.
CPC ....... *G01N 21/6456* (2013.01); *A61B 5/0071* (2013.01); *A61B 5/6886* (2013.01);
(Continued)

(58) Field of Classification Search
CPC .......... G01N 21/6456; G01N 21/6428; G01N 2021/6439
See application file for complete search history.

(56) References Cited

U.S. PATENT DOCUMENTS 5,749,830 A * 5/1998 Kaneko .............. A61B 1/00082
348/E5.038
6,280,378 B1    8/2001 Kazuhiro et al.
(Continued)

FOREIGN PATENT DOCUMENTS

| EP | 1 829 473 A2 | 9/2007 |
| EP | 2 412 296 A1 | 2/2012 |
| EP | 2 505 988 A1 | 10/2012 |

OTHER PUBLICATIONS

International Search Report dated Sep. 2, 2016 in PCT/FR2016/051114 filed May 11, 2016.

*Primary Examiner* — David P Porta
*Assistant Examiner* — Djura Malevic
(74) *Attorney, Agent, or Firm* — Oblon, McClelland, Maier & Neustadt, L.L.P.

(57) ABSTRACT

A method for correcting a fluorescence image of an object, for example a biological tissue that can include fluorescent agents. The distance between a fluorescence probe generating the fluorescence image and the object examined is measured. This distance is used to apply a correction function to the fluorescence image. The method may find application in perioperative fluorescence imaging for diagnosis and monitoring of evolution of pathologies, for example of cancers.

19 Claims, 8 Drawing Sheets

(51) Int. Cl.
  *G01N 21/27* (2006.01)
  *G01S 13/08* (2006.01)
  *A61B 1/04* (2006.01)

(52) U.S. Cl.
  CPC ....... *G01N 21/276* (2013.01); *G01N 21/6428* (2013.01); *G01S 13/08* (2013.01); *A61B 1/043* (2013.01); *G01N 2021/6439* (2013.01); *G01N 2021/6471* (2013.01)

(56) References Cited

U.S. PATENT DOCUMENTS

| | | | | |
|---|---|---|---|---|
| 7,286,287 B1* | 10/2007 | Ofner | ................... | G02B 7/002 |
| | | | | 359/404 |
| 8,654,185 B2* | 2/2014 | Ono | ...................... | A61B 1/05 |
| | | | | 348/68 |
| 8,831,374 B2* | 9/2014 | Watanabe | ............ | A61B 1/0638 |
| | | | | 382/128 |
| 2004/0008394 A1* | 1/2004 | Lange | .................. | G01S 7/4816 |
| | | | | 359/237 |
| 2007/0197874 A1 | 8/2007 | Ishihara | | |
| 2009/0262891 A1* | 10/2009 | Zhang | ................... | G01B 15/00 |
| | | | | 378/57 |
| 2012/0076434 A1 | 3/2012 | Watanabe et al. | | |
| 2012/0249862 A1 | 10/2012 | Makino | | |
| 2013/0113907 A1* | 5/2013 | Ono | ...................... | A61B 1/05 |
| | | | | 348/68 |
| 2013/0200273 A1 | 8/2013 | Watanabe et al. | | |
| 2013/0200274 A1 | 8/2013 | Watanabe et al. | | |
| 2013/0200275 A1 | 8/2013 | Watanabe et al. | | |
| 2013/0201320 A1* | 8/2013 | Watanabe | ............ | A61B 1/0638 |
| | | | | 348/77 |
| 2013/0293702 A1* | 11/2013 | Xin | ...................... | G01J 3/0208 |
| | | | | 348/135 |
| 2014/0267603 A1* | 9/2014 | Kerdok | ............... | H04N 13/122 |
| | | | | 348/43 |
| 2015/0286340 A1* | 10/2015 | Send | ..................... | G01S 17/46 |
| | | | | 345/175 |
| 2015/0359504 A1* | 12/2015 | Zhou | ..................... | A61B 6/547 |
| | | | | 378/38 |
| 2016/0127664 A1* | 5/2016 | Bruder | ................. | G01S 7/4816 |
| | | | | 463/30 |
| 2017/0074652 A1* | 3/2017 | Send | ..................... | G01J 3/513 |
| 2017/0363741 A1* | 12/2017 | Send | ..................... | G01S 17/46 |

* cited by examiner

METHOD OF CORRECTING A FLUORESCENCE IMAGE

TECHNICAL FIELD

The field of the invention is imaging, and in particular pre-op fluorescence imaging for diagnosing and tracking the evolution of pathologies or treatments in the medical field.

PRIOR ART

Fluorescence imaging is a technique allowing fluorescent markers to be located in an animal or human body. One of its main applications is the location of fluorescent markers, or fluorophores, the latter targeting cells of interest, for example cancer cells. The protocol consists in injecting these markers into the organism before a surgical intervention, so that, during the intervention, the practitioner is able to see the cancer cells via a fluorescence image. Because it allows an image indicating the location of various cancerous zones to be acquired, pre-op fluorescence imaging allows information that was previously unavailable to the practitioner to be obtained and is a useful complement, or even an alternative, to the use of radioactive tracers. Another application is as an aid in interventions in reconstructive and plastic surgery, in cardiovascular surgery, in surgery on the lymphatic system, or in hepatic surgery, in which fluorescence imaging allows visual inspection of lymphatic drainage, of perfusion or of the distribution of blood vessels.

The principle of fluorescence imaging is to illuminate a field of observation using a light source in an excitation spectral band of the fluorophores. Under the effect of this illumination, the fluorophores emit fluorescence radiation, in a fluorescence spectral band. This radiation may be captured by a fluorescence probe, so as to form a fluorescence image in which various fluorescent zones appear. It is then possible to acquire a visible image of the observed field, and to superpose the fluorescence image on this visible image.

The fluorescence probe may be a compact assembly, including the excitation light source, and be held by a practitioner, at a distance of a few tens of centimeters from an examined tissue. However, depending on the position of the probe with respect to the tissue, the brightness of the fluorescence images may vary, in particular as a function of the distance between the probe and the observed tissue. Thus, although such images allow fluorescent zones to be located correctly, they are difficult to compare, from a quantitative point of view, with one another, unless the practitioner is required to place the fluorescence probe at a fixed distance with respect to the observed tissue. Certain devices are based on such a constraint and enable a quantitative approach only at the price of requiring the probe to be placed at a set distance from the observed tissue. This is a substantial drawback.

Document U.S. Pat. No. 8,606,350 aims to solve this problem, by using a fluorescence probe able to measure the distance separating it from an examined biological tissue. It is then possible to correct the fluorescence image delivered by this probe using this distance. The objective is to enable quantitative fluorescence, in particular making it possible to compare and quantify the brightness levels of the observed fluorescent zones. To do this, a fluorescence image is acquired and this image is corrected by multiplying it by the previously measured distance. However, this approach is based on the assumption of an inversely proportional relationship between the magnitude of the measured signal and distance, and does not allow the influence of distance on the obtained fluorescence image to be completely eliminated. Document EP1829473 follows a similar approach, describing a fluorescence endoscope including a unit for measuring the distance between the endoscope and the surface of an observed sample. The distance measured using the unit for measuring distance is used to correct a fluorescence image acquired by the fluorescence endoscope, in particular by dividing said fluorescence image by the square of the measured distance.

Document EP 2505988 describes a device for analyzing the fluorescence of a sample. This device allows an image of fluorescence radiation emitted by the sample to be acquired, this image being corrected using a reference image that is obtained by replacing the sample with a reference sample, the latter for example being an acrylic plate.

Document US2013/113907 describes a fluorescence endoscope each acquired image of which is divided by a reference image that is obtained using a reference sample, in order to correct the vignetting effects of lenses of the endoscope. A similar approach is described in U.S. Pat. No. 5,749,830.

Document U.S. Pat. No. 6,280,378 describes a fluorescence endoscope, in which the fluorescence image of a sample is normalized by an image of the sample, the latter being illuminated by light at the fluorescence wavelength. The effectiveness of such a method depends on the optical properties of the sample, and requires the latter to be illuminated by light at the fluorescence wavelength. Similarly, document EP2412296 describes normalization of a fluorescence image of a sample by a visible image of the same sample. The correction therefore depends on the reflective and backscattering properties of the sample, this possibly complicating interpretation of the results.

The inventors propose to improve the methods described in the aforementioned documents by providing an improved method for correcting a fluorescence image of a sample, which is independent of the optical properties of the observed sample.

SUMMARY OF THE INVENTION

One subject of the invention is a method for correcting a fluorescence image, comprising the following steps:
  illuminating an object using an excitation light source;
  detecting fluorescence radiation with a fluorescence-image sensor, the fluorescence radiation being emitted by the object under the effect of said illumination; and
  acquiring said fluorescence image with said fluorescence-image sensor on the basis of the detected fluorescence radiation,
the method being characterized in that it comprises applying a correction function to the fluorescence image, said correction function using an illuminance image representative of the spatial distribution of an illuminance produced, on the object, by the excitation light source.

According to one embodiment, the method also includes a step of measuring a distance between the excitation source and the object, the correction function being dependent on this distance since it uses an illuminance image associated with said measured distance. Preferably, the correction function is such that two illuminance images respectively associated with two different measured distances are different from each other.

The method may include the following features, independently or in any technically producible combinations:
  the correction function may apply a term-by-term ratio of the fluorescence image to said illuminance image;

the illuminance image may be normalized, in particular by a maximum brightness level of this illuminance image;

the fluorescence image is acquired in an exposure time and the correction function is also able to normalize the fluorescence image with respect to a reference exposure time;

the correction function takes into account the square of the measured distance and the square of a reference distance;

the method includes a step of selecting the reference distance depending on the fluorescence image;

the correction function includes a product of the fluorescence image multiplied by a ratio between the square of the measured distance and the square of the reference distance;

the distance between the excitation light source and the object is measured by means of a rangefinder that is able to emit a wave in the direction of the object and to detect a wave reflected by said object, depending on which wave said distance is measured. The rangefinder may then be a laser rangefinder, an ultrasonic rangefinder or a microwave rangefinder;

the distance between the excitation light source and the object is measured by an optical rangefinder including a matrix-array photodetector that is able to determine a plurality of distances respectively between the excitation light source and a plurality of surface elements forming a surface of the object. In this case, the correction function may include a term-by-term product of the fluorescence image multiplied by a ratio between the square of the distance measured between the excitation source and a surface element and the square of a reference distance;

the distance between the excitation light source and the object is measured by an autofocus system that is able to automatically establish a focus distance of the fluorescence-image sensor with respect to the object;

the method includes a step of acquiring a visible image of the object using a visible-image sensor.

Another subject of the invention is a device for acquiring a fluorescence image including:

an excitation light source able to illuminate an object in an excitation spectral band;

a fluorescence-image sensor able to collect fluorescence radiation emitted by said object, in a fluorescence spectral band, under the effect of the illumination by the excitation light source, the fluorescence-image sensor being able to acquire a fluorescence image on the basis of the collected fluorescence radiation; and a rangefinder for measuring a distance between the excitation light source and the object, the rangefinder being able to emit an optical wave in the direction of the object and to detect an optical wave reflected by said object, depending on which wave said distance is measured, the acquiring device being characterized in that it is also includes one or more of the following features, individually or in combination:

the fluorescence-image sensor is centered on an optical axis and the rangefinder is able to emit said optical wave along said optical axis;

the fluorescence-image sensor includes a focusing optical system and the rangefinder is configured to emit an optical wave in the direction of the object, said wave being centered using this optical system;

the device includes a selector of a reference distance, in order to store said reference distance in a memory;

the rangefinder includes a matrix-array photodetector that is able to determine a plurality of distances respectively between the excitation source and a plurality of surface elements forming the surface of the object;

the device includes a processor able to implement the method for correcting said fluorescence image such as described above.

FIGURES

Figure 6A:
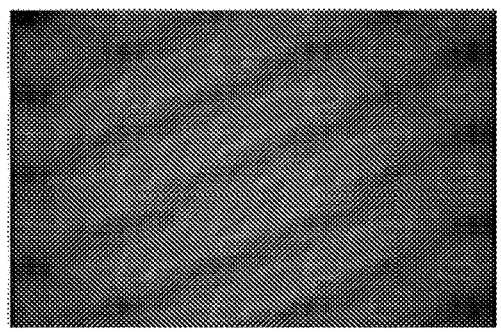
Figure 6B:
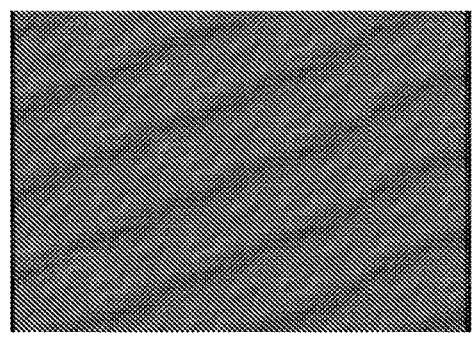
Figure 6C:
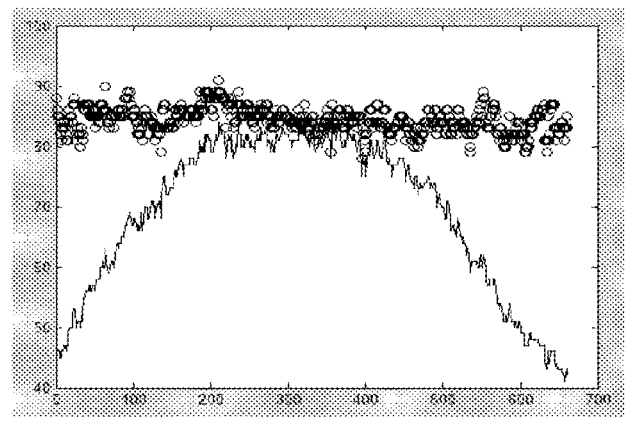

FIG. 6A shows a uncorrected fluorescence image. FIG. 6B shows a fluorescence image corrected according to a first embodiment of a correcting method according to the invention. FIG. 6C shows profiles of the brightness of the pixels of the images 6A and 6B along a horizontal line passing through the center of this image.

FIGS. 7A, 7B, 7C and 7D are flow charts showing the steps of correcting methods according to a first, second, third and fourth embodiment, respectively.

FIGS. 8A, 8B, 8C and 8D are images obtained without correction, and with implementation of a correcting function according to a first, third and fourth embodiment, respectively.

Figure 9:
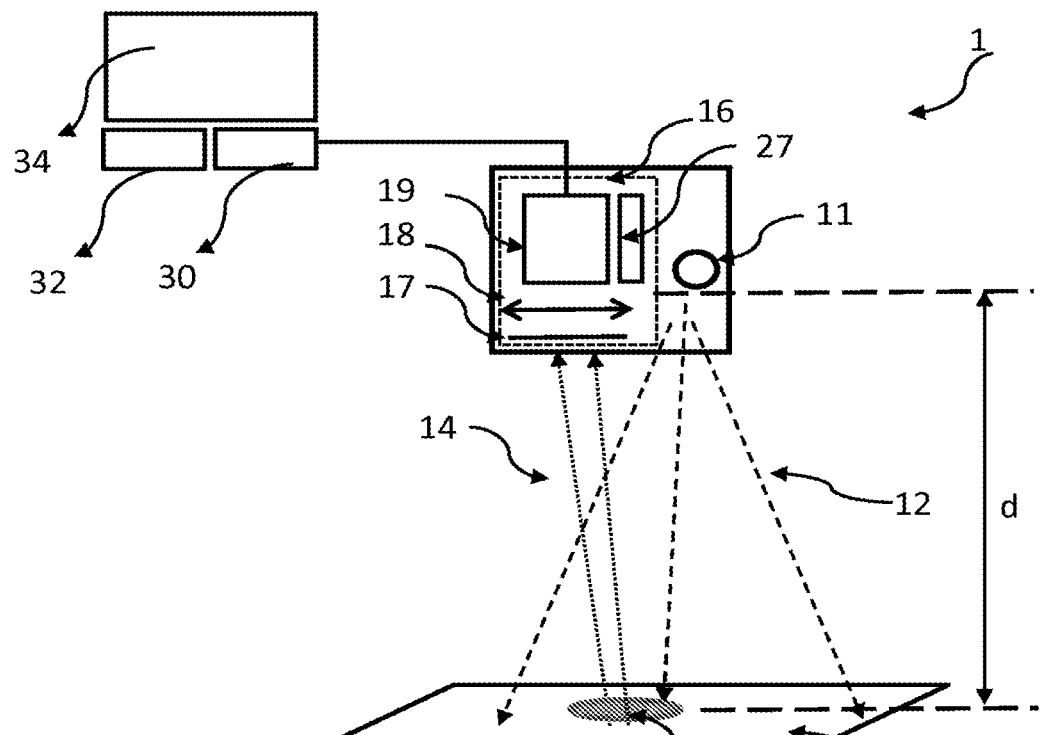

FIG. 9 shows a second embodiment of a device according to the invention.

Figure 10:
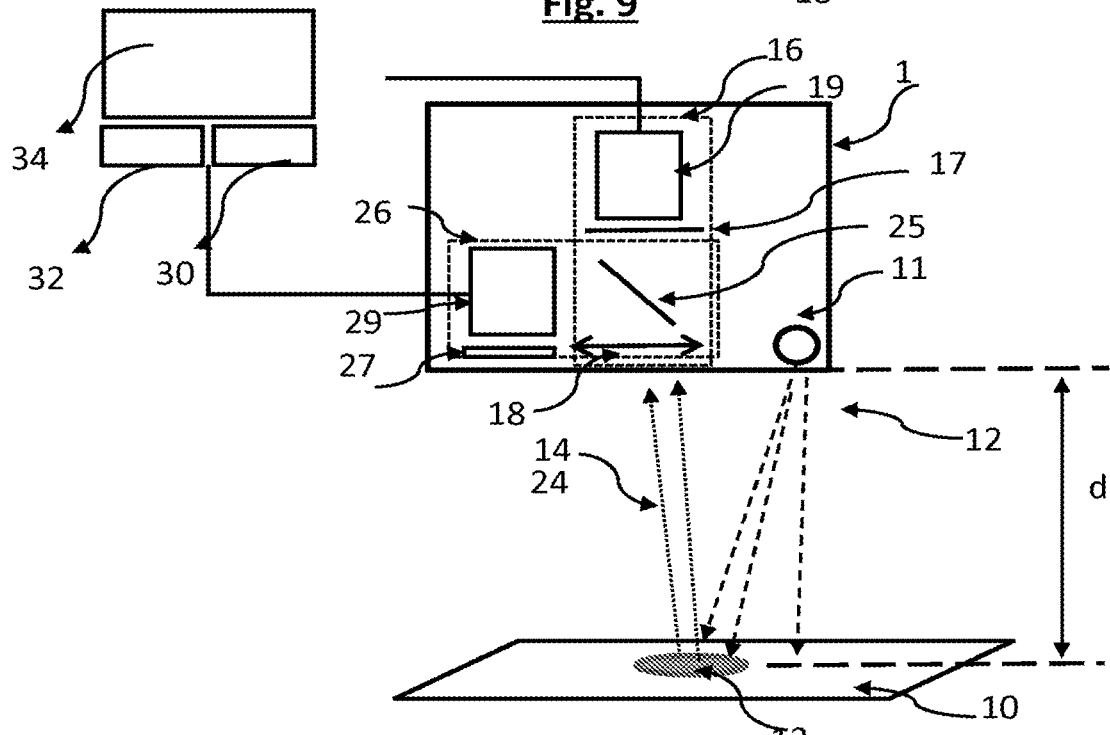

FIG. 10 shows a third embodiment of a device according to the invention.

Figure 11:
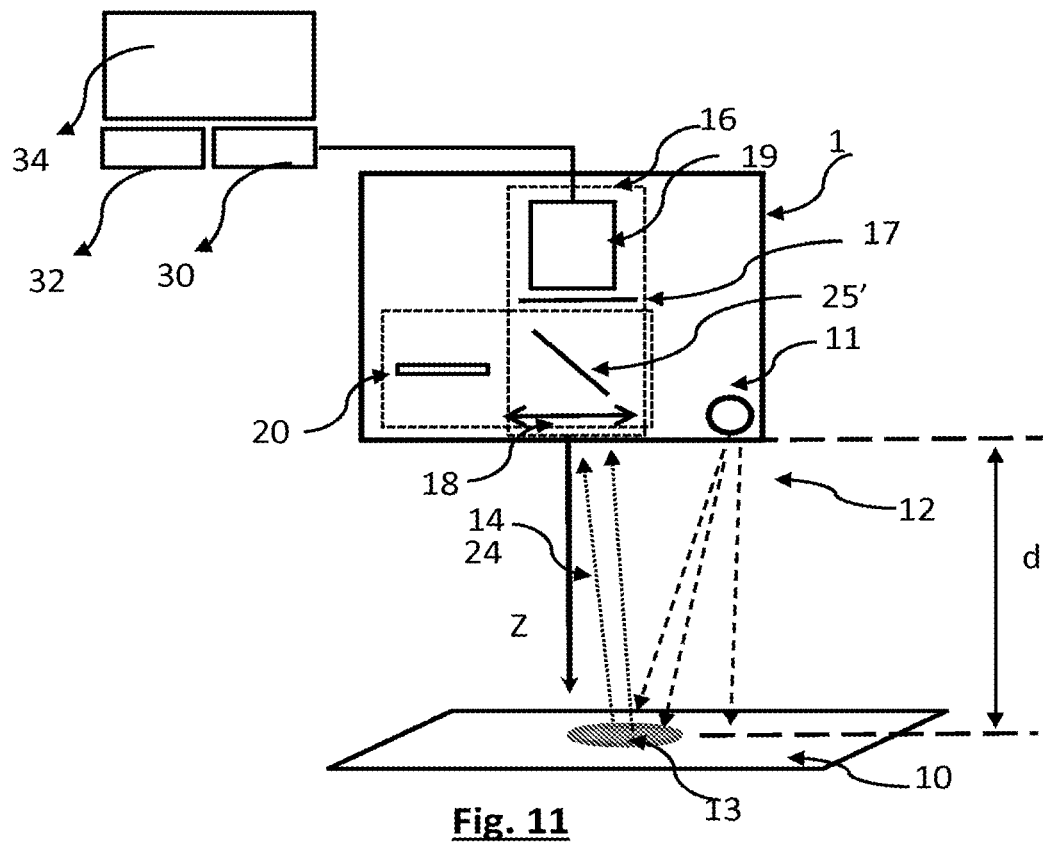

FIG. 11 shows a fourth embodiment of a device according to the invention.

Figure 12:
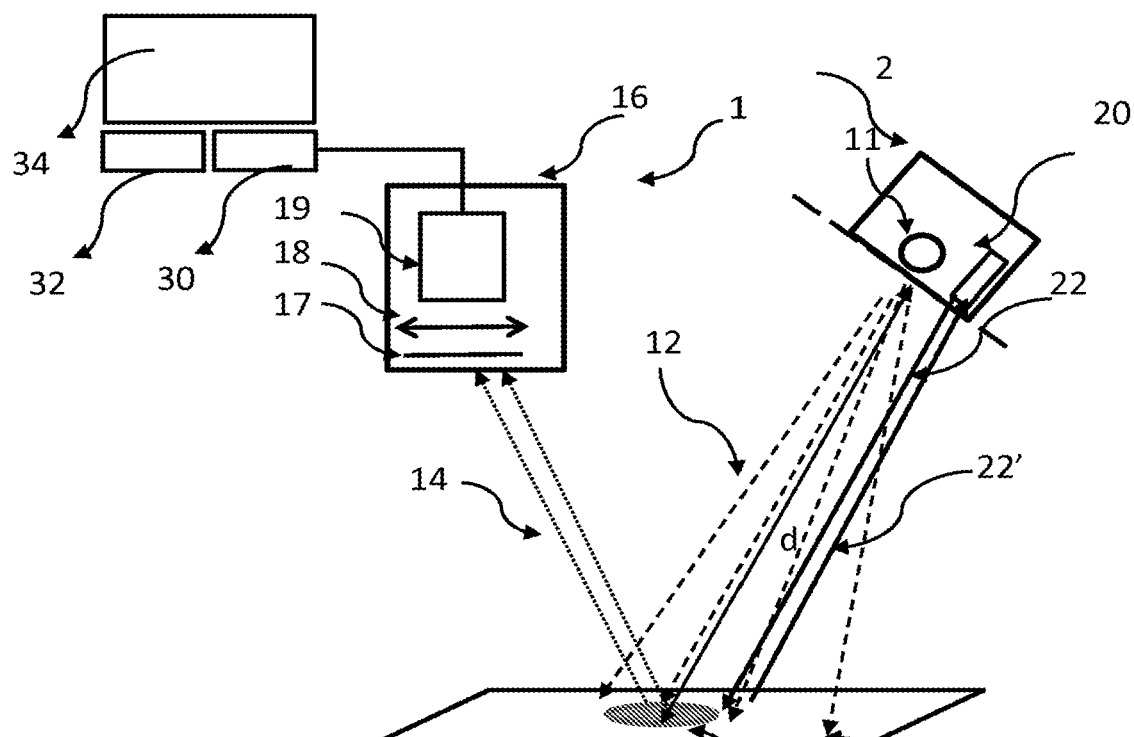

FIG. 12 shows a fifth embodiment of a device according to the invention.

Figure 13:
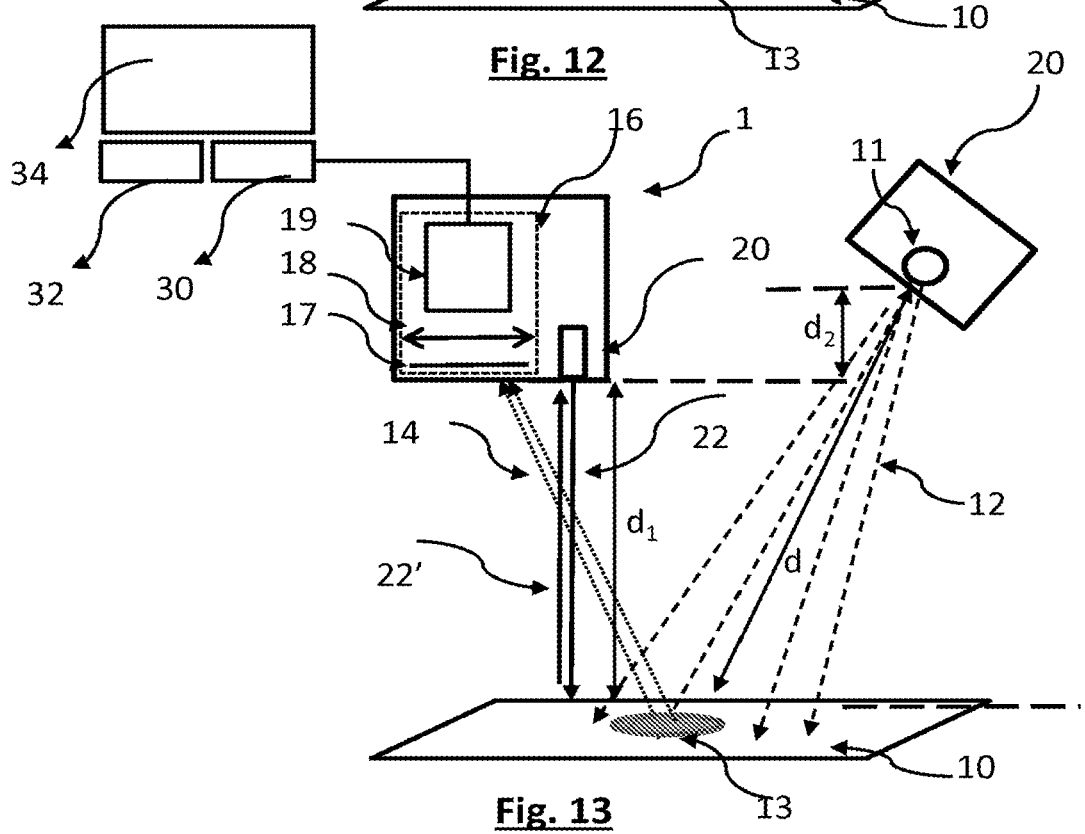

FIG. 13 shows a sixth embodiment of a device according to the invention.

DESCRIPTION OF PARTICULAR EMBODIMENTS

Figure 1:
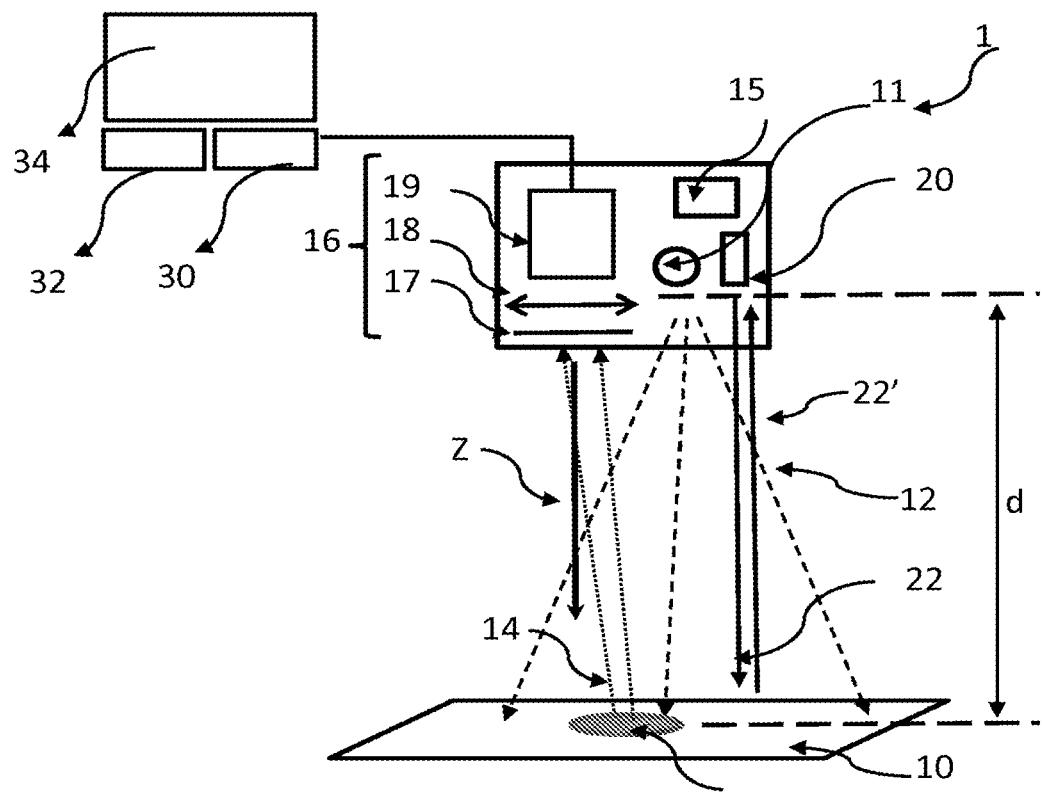
FIG. 1 shows a device according to a first embodiment of the invention.

FIG. 1 shows a first embodiment. A fluorescence probe 1 includes an excitation light source 11 that is able to emit an excitation light beam 12, in an excitation spectral band $\lambda_{ex}$, so as to illuminate an object 10. The object 10 is a sample to be characterized, for example a biological tissue, exposed to the probe 1 during a surgical intervention. The light source is for example a light-emitting diode, optionally comprising an excitation filter that is able to block wavelengths outside of the excitation spectral band $\lambda_{ex}$. It may also be a laser diode, or one end of an excitation optical fiber, the other end of this fiber being placed facing a light source.

The excitation source 11 may be divided into a plurality of elementary excitation sources 11.1, 11.2 . . . 11.n.

The probe also includes an emission-image sensor 16, comprising a focusing optical system 18 and a matrix-array photodetector 19. The emission-image sensor 16 is able to form an image $I_{em}$ of emission radiation 14 produced by the object 10 under the effect of the illumination by the excitation beam 12.

This emission radiation 14 may be emitted by the object in the same spectral band as the excitation spectral band. It is then a question of radiation reflected by the object, or of radiation backscattered by the object.

The emission radiation 14 may be emitted by the object in a fluorescence spectral band $\lambda_{fluo}$ that is different from the excitation spectral band $\lambda_{ex}$. It is then a question of fluorescence radiation. The emission-image sensor is then a fluorescence-image sensor, able to form an image $I_{fluo}$ of fluorescence radiation 14 produced by the object 10, in said fluorescence spectral band, under the effect of the illumination by the excitation beam 12.

In the following examples, the particular case of acquisition and correction of a fluorescence image is systematically addressed, though the principles described apply to any type of image $I_{em}$ emitted by the object, whatever the emission spectral band, and in particular to an image of radiation reflected by the object or to an image of radiation backscattered by the object.

When the probe includes a plurality of elementary excitation sources, the latter may be distributed around the fluorescence-image sensor 16.

The fluorescence-image sensor 16 preferably includes a filter 17. The filter 17 is a passband filter centered on the fluorescence spectral band $\lambda_{fluo}$, so as to block wavelengths outside of this fluorescence spectral band.

The focusing optical system 18 is configured to form an image $I_{fluo}$ of the fluorescence radiation 14 on the matrix-array photodetector 19. It may in particular be a question of an objective. The matrix-array photodetector includes a plurality of pixels, such that each pixel of the fluorescence image $I_{fluo}$ is optically coupled, by the focusing optical system 18, to a surface element δS of the object 10, such a surface element forming a portion of that surface S of the object 10 which is placed facing the probe 1.

The fluorescence sensor 16 has an optical axis Z that is defined by the focusing optical system 18 and the photodetector 19.

The matrix-array photodetector 19 is a CCD (charge-coupled device) sensor or a CMOS (complementary metal-oxide semiconductor) sensor.

The object 10 includes one or more exogenous or endogenous fluorophores. In the case where the fluorophores are endogenous, autofluorescence is spoken of. Exogenous fluorophores are injected beforehand into the object, so as to specifically fix to targets, for example cancerous cells. Each fluorophore is able to emit fluorescence radiation 14, in a fluorescence spectral band $\lambda_{fluo}$, when it is illuminated by excitation radiation 12, in an excitation spectral band $\lambda_{ex}$. For example, when the fluorophore used is indocyanine green (ICG), the excitation spectral band may be comprised between 750 nm and 800 nm, the fluorescence spectral band being comprised between 820 nm and 870 nm.

The fluorescence image $I_{fluo}$ includes pixels r. The value of each pixel $I_{fluo}(r)$ corresponds to the intensity of the fluorescence radiation emanating from a surface element δS(r') of the object, this surface element being optically coupled to this pixel. The positions r and r' respectively designate the coordinates of a pixel in the fluorescence image $I_{fluo}$ and the coordinates of a surface element on the surface S of the object 10. Each position r and/or r' may correspond to an abscissa x and an ordinate y, such that r=(x, y) and/or r'=(x', y').

The intensity of the fluorescence radiation emanating from each surface element may also be qualified apparent fluorescence intensity, the fluorescence possibly being produced on the surface of the object or at depth, this depth generally being limited to a few centimeters. The fluorescence image $I_{fluo}$ generated by the image sensor 16 gives the appearance that the fluorescence originates from the surface S of the object 10, whereas it may be generated at depth.

A processor 30 is able to process the fluorescence images $I_{fluo}$ formed by the image sensor 16. It is for example a question of a microprocessor placed in a desktop computer. In particular, the processor is a microprocessor 30 that is connected to a programmable memory 32 in which is stored a sequence of instructions for performing the image-processing operations and computations described in this description. The microprocessor 30 may be connected to a display screen 34.

When the object includes a fluorescent zone 13 that is located in the field of observation of the probe 1, this fluorescent zone appears, in the fluorescence image $I_{fluo}$, in the form of a region of interest Ω. The region of interest Ω may be characterized by a fluorescence signal $S_{fluo}$ representative of the brightness of the pixels that compose it.

The probe 1 also includes a distance detector, taking the form of a rangefinder 20, intended to measure a distance d between the excitation light source 11 and the object 10. This rangefinder 20 may be an optical, ultrasonic or microwave rangefinder. Generally, the rangefinder 20 emits a wave, called the rangefinding wave 22 toward the object 10, then detects a wave 22' reflected by the object, on the basis of which a measurement of distance is carried out. The wave 22 may be an optical wave in the infrared or visible spectrum, or an acoustic wave or even an electromagnetic microwave. In this example, the rangefinder 20 is a laser rangefinder. The rangefinder may in particular be a time-of-flight rangefinder, able to determine a length of time between the emission of the rangefinding wave and the detection of the rangefinding wave reflected by the object.

Figure 2:
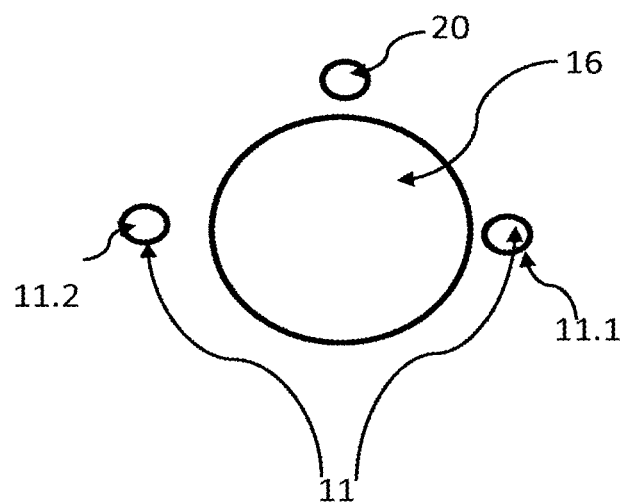
FIG. 2 shows a variant of this device.

In the examples shown in FIGS. 1 and 2, the image sensor 16, the excitation light source 11 and the rangefinder 20 are integrated into the probe 1.

The probe 1 is generally placed at a distance from the object 10 comprised between 10 cm and 30 or even 50 cm or more. It may be moved manually by a practitioner, so as to locate any fluorescent zones 13 in the object 10. These fluorescent zones may be located on the surface or a few millimeters, or even centimeters, below the surface of the object. The practitioner may for example hold such a probe in his hand, and scan the operating field in order to perform a complete examination.

The illuminance φ produced by the excitation light source 11 on the examined object is often spatially nonuniform, and includes zones that are more brightly lit than others, defining an illuminance image. It will be recalled that illuminance φ corresponds to an amount of light per unit time and area. The illuminance image generally depends on the distance d between the light source 11 and the object 10 and may vary significantly between two different distances.

FIG. 2 shows a front view of a variant in which the excitation source 11 includes two elementary excitation sources 11.1 and 11.2 that are placed on either side of the fluorescence sensor 16. Each of these elementary excitation sources includes a plurality of optical fibers, from ends of which the excitation beam 12 is emitted.

Figure 3A:
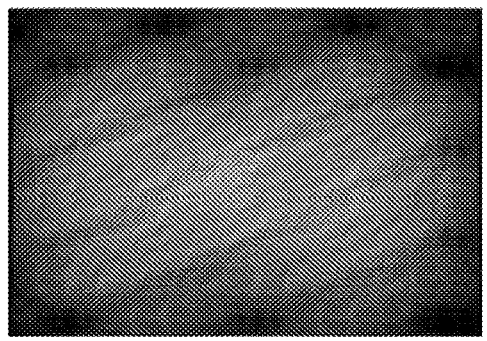
FIG. 3A shows an illuminance image when the illuminance source is placed at a distance of 10 cm from the screen.
Figure 4A:
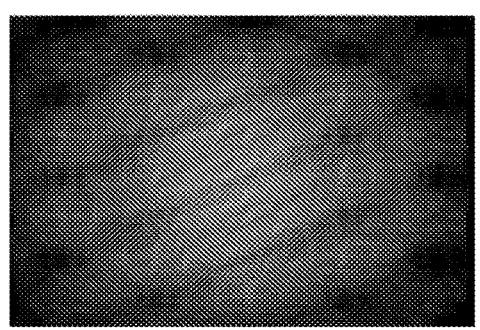
FIG. 4A shows an illuminance image when the illuminance source is placed at a distance of 20 cm from the screen.
Figure 5A:
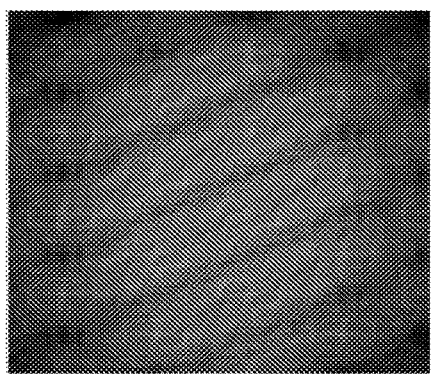
FIG. 5A shows an illuminance image when the illuminance source is placed at a distance of 30 cm from the screen.

FIGS. 3A, 4A and 5A show, for various distances d, the spatial distribution of illuminance, in a plane perpendicular to the axis of propagation of the excitation beam 12, with such a configuration. The two excitation sources 11.1 and 11.2 consist of the end of two optical fibers that are connected to a laser source emitting at an excitation wavelength of 750 nm.

Figure 3B:
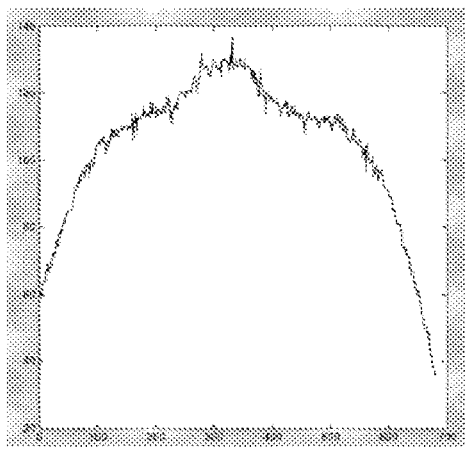
FIG. 3B shows a profile of the brightness of the pixels of the image 3A along a horizontal line passing through the center of this image.
Figure 4B:
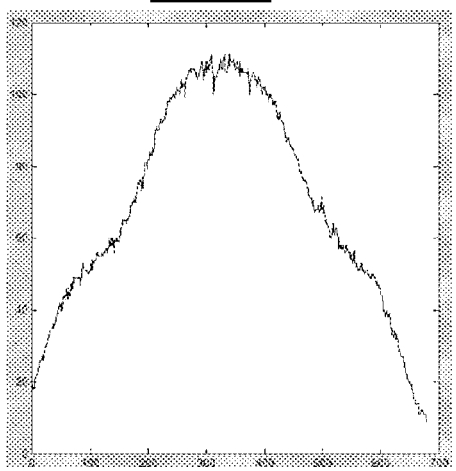
FIG. 4B shows a profile of the brightness of the pixels of the image 4A along a horizontal line passing through the center of this image.
Figure 5B:
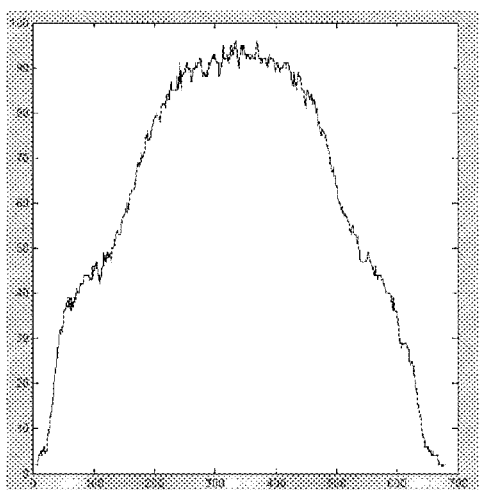
FIG. 5B shows a profile of the brightness of the pixels of the image 5A along a horizontal line passing through the center of this image.

To produce these figures, a uniform fluorescent screen was placed facing the probe, the distance between the screen and the probe being 10 cm, 20 cm and 30 cm, respectively. FIGS. 3B, 4B and 5B show the horizontal profile, passing through the center of the image, for each configuration.

The inventors have observed that, whatever the distance, the illuminance is nonuniform. It is maximum at the center of the observed field, and decreases significantly as the edges of the image are approached. Moreover, the inventors have observed that the spatial distribution of the illuminance varies as a function of distance, in particular in pre-op applications, in which the distance between the probe and the observed scene may vary between a few centimeters and a few tens of centimeters.

This spatial nonuniformity complicates correct quantification of the fluorescence signals $S_{fluo}$, the intensity of the fluorescence radiation 14 varying linearly with the illuminance $\phi$ produced by the excitation beam 12. Thus, with such a spatially nonuniform illuminance, the signal-to-noise ratio of the probe is nonuniform: it is clearly higher in the central zone of the observed field than in the peripheral zone of this field.

According to a first embodiment, in order to remedy this problem, the inventors propose to apply a correction function $f_d$ that is dependent on said distance d to each fluorescence image. This function corrects the fluorescence image $I_{fluo}$ so as to obtain a corrected fluorescence image $I'_{fluo}$ such that:

$$I'_{fluo} = f_d(I_{fluo}) = \frac{I_{fluo}}{M_d}, \quad (1a)$$

$M_d$ corresponding to an illuminance image produced by the light source 11 at the distance d. This illuminance image is representative of the spatial distribution of the luminance produced by the excitation source in a plane located at a distance d from the latter.

The ratio $$\frac{I_{fluo}}{M_d}$$

implies that the brightness of each pixel of coordinate (r) of the fluorescence image $I_{fluo}$ is divided by the brightness of a pixel of the same coordinate of the illuminance image $M_d$. In other words, it is a question of a term-by-term ratio between two matrices such that the value of each pixel r of the corrected image is:

$$I'_{fluo}(r) = f_d(I_{fluo}(r)) = \frac{I_{fluo}(r)}{M_d(r)}.$$

With each distance d is associated an illuminance image $M_d$, the latter being determined during a calibration phase, by replacing the object 10, with a uniform screen, for example a black screen, or, better still, a fluorescent screen, the fluorescence being spatially uniform. Such a fluorescent screen may consist of a material that is naturally fluorescent in the fluorescence wavelength band $\lambda_{fluo}$ of the fluorescence image sensor 16. It may for example be a question of a polymer, for example a plate of the polymethyl methacrylate (PMMA) sold under the reference Altuglas (registered trademark) 25001.

The image formed on this screen, placed a distance d from the light source 11, then corresponds to the illuminance image $M_d$ associated with said distance d. It includes light zones and dark zones, representing the, often nonuniform, spatial distribution of the illuminance $\phi$ as a function of the distance d. A plurality of illuminance images $M_{d1} \ldots M_{dn}$ may be produced by considering various distances $d_1 \ldots d_n$, for example every 1 or 2 cm. Images corresponding to intermediate distances, between two distances $d_i$, $d_{i+1}$, may be obtained by interpolation between two images $M_{di}$ and $M_{di+1}$. As many illuminance images $M_d$ as distances d considered are then stored in memory. The illuminance images $M_{d'}$ and $M_{d''}$ respectively associated with two different distances d' and d'' are generally different. The various images $M_d$, corresponding to each distance considered, may be stored in a memory 32 connected to the processor 30.

An illuminance image $M_d$ may also be produced for various configurations of the focusing optical system 18 used in the fluorescence image sensor 16, and in particular depending on a magnification G of this optical system, so as to generate illumination images $M_{d,G}$ corresponding to various pairs of values of the distance d and of the magnification G.

Each illuminance image $M_d$ or $M_{d,G}$ makes it possible to take account of vignetting affecting the fluorescence image sensor 16, or, more generally, any nonuniformity in the response function of this sensor, whether it be due to the objective 18 or to the matrix-array photodetector 19, or even to the filter 17. Under these conditions, each illuminance image $M_d$ or $M_{d,G}$ may be qualified a blank image, because it corresponds to a calibration image, on a uniform background, of the probe when the light source 11 is activated.

Each fluorescent zone 13 of the object may then be characterized not only by its position and its spatial extent, such as it appears in the region of interest $\Omega$ of the fluorescence image, but also by a piece of quantitative information, taking the form of a signal $S_{fluo}$ representative of the brightness of the pixels making up this region of interest. If $\Omega$ defines the spatial extent of said region of interest in the fluorescence image $I'_{fluo}$, the quantitative information corresponds to the fluorescence signal $S_{fluo}$. The latter may be defined, non-exhaustively, by one of the following expressions:

- the maximum brightness in the region of interest $\Omega$: $S_{fluo} = \max_\Omega(i'_{fluo}(r))$;
- the mean brightness in the region of interest $\Omega$: $S_{fluo} = \text{mean}_\Omega(i'_{fluo}(r))$, where mean designates the mean operator;
- the total brightness of the region of interest $\Omega$: $S_{fluo} = \int_\Omega i'_{fluo}(r)$; $I'_{fluo}(r)$ designates the brightness of a pixel of coordinate r in the corrected fluorescence image $I'_{fluo}$.

The practitioner is then able to compare the various fluorescence zones not only depending on the extent of the zones of interest in the fluorescence image, but also depending on their respective brightnesses, the correction function $f_d$ having corrected for the spatial nonuniformity of the illuminance. The correction may be carried out in real-time, i.e. at the rate of acquisition of the fluorescence images, or during post processing.

Use of such an illuminance image $M_d$ has the advantage of taking into account, during the application of the correction function, the spatial distribution of the illuminance, but also the variation in the illuminance as a function of the distance d between the excitation source and the object. Now, the intensity of the fluorescence light 12 emitted by the object 10 is proportional to the illuminance. Thus, by implementing a correction function taking into account an illuminance image, the process method allows both the spatial nonuniformity of the illuminance and the variation of the latter, as a function of the distance between the excitation light source 11 and the object 10, to be corrected.

Such a correction allows a corrected fluorescence image $I'_{fluo}$ to be obtained in which the value of each pixel $I'_{fluo}(r)$ is representative of an apparent concentration of fluorophores in that surface element $\delta S(r')$ of the object which is optically coupled to said pixel r. Specifically, as indicated above, $I_{fluo}(r)$ corresponds to the intensity of the fluorescence light emanating from the surface element $\delta S(r')$ conjugated with the pixel r of the image $I_{fluo}$. Thus, $$I_{fluo}(r) \propto \phi_d(r') \times \eta \times c(r') \quad (1')$$

where:
- $\phi_d(r')$ designates the illuminance to which the surface element $\delta S(r')$ of the object is subject, at the distance d from the excitation source;
- $\eta$ designates the quantum yield of the fluorophore generating the fluorescence signal; and
- $c(r')$ designates the apparent concentration of the fluorophore in the surface element $\delta S(r')$.

The expression "apparent concentration" means the fluorophore concentration causing the fluorescence signal emanating from the surface element $\delta S(r')$.

During the acquisition of the illuminance image $M_d$, using a fluorescent screen, each pixel of the image $M_d$ is such that:

$$M_d(r) \propto \phi_d(r') \times \eta \times c_0(r') \quad (1'')$$

where:
- $\phi_d(r')$ designates the illuminance on the fluorescent screen;
- $\eta$ designates the quantum yield of the fluorophore generating the fluorescence signal; and
- $c_0(r')$ designates the apparent concentration of fluorophores in the calibration screen, at the point r' conjugated with the point r of the image. This concentration is preferably uniform in the screen, so that $c_0(r')=c_0$.

It will be noted that the same excitation source is used in the respective acquisitions of the fluorescence image and the illuminance image. The illuminance produced by the excitation source at the distance d, $\phi_d(r')$, is therefore the same during the acquisition of these two images.

The corrected image $I'_{fluo}$, taking the form of a term-by-term ratio between the fluorescence image $I_{fluo}$ and the illuminance image $M_d$ is therefore such that:

$$I'_{fluo}(r) = f_d(I_{fluo}(r)) = \frac{I_{fluo}(r)}{M_d(r)} \propto \frac{c(r')}{c_0} \propto c(r') \quad (1''')$$

Thus, the corrected image represents the spatial distribution of the concentration of the fluorophore on the surface S of the object 10.

The fluorescence signal $S_{fluo}$, such as defined above, associated with a fluorescence zone 13, then represents, depending on how it is defined, the total or mean concentration of fluorophores in the zone in question.

According to one variant, each illuminance image is normalized. The normalization may be carried out by taking into account the value of the pixels in which the illuminance is maximum. Thus, the normalization may consist in performing the following operation:

$$M'_d(r) = \frac{M_d(r)}{\max(M_d(r))}$$

- $M'_d(r)$ representing the value of the pixel of coordinate r of the normalized illuminance image $M'_d$;
- $M_d(r)$ representing the value of the pixel of coordinate r of the illuminance image $M_d$; and
- $\max(M_d(r))$ representing the value of the pixel of the illuminance image $M_d$ representative of the maximum illuminance.

In this variant, the correction function allows a corrected fluorescence image $I'_{fluo}$ to be established such that:

$$I'_{fluo} = f_d(I_{fluo}) = \frac{I_{fluo}}{M'_d}, \quad (1b)$$

One advantage of such a normalization is that it makes it possible to independently correct for the intensity of the excitation source, and any fluctuations therein.

FIG. 6A shows an uncorrected fluorescence image $I_{fluo}$, when the distance between the source and a uniform screen is 20 cm, using a normalized illuminance image $M'_d$. FIG. 6B shows a fluorescence image $I'_{fluo}$ corrected by implementing equation (1b). FIG. 6C shows a horizontal profile, passing through the center of the image, for each of these images. It may be seen that the profile associated with the corrected image represents, excluding fluctuations, a uniform fluorescence signal, corresponding to the actual uniform fluorescence of the screen, which is not the case in the uncorrected image.

According to another variant of this first embodiment, the correction function is established for a distance at which the illuminance is considered to be sufficiently representative of a certain distance range. In this variant, the correction function f does not vary with distance, and may use the same illuminance image M, whether normalized or not, whatever the distance used. In this case:

$$I'_{fluo} = f(I_{fluo}) = \frac{I_{fluo}}{M}, \quad (1c)$$

The implementation of the corrections, whatever they may be, described with reference to this first embodiment assumes, preferably, that the relative position of the fluorescence image sensor and the excitation light source is known and that it corresponds to the conditions under which the illuminance images $M_d$ were established. Thus, such a correction is particularly suitable for probes incorporating, in one and the same body, the light source and the fluorescence image sensor, the relative position of the light source and fluorescence image sensor being fixed. The devices shown in FIGS. 1, 2, 9, 10 and 11 correspond to this particular case.

Figure 7A:
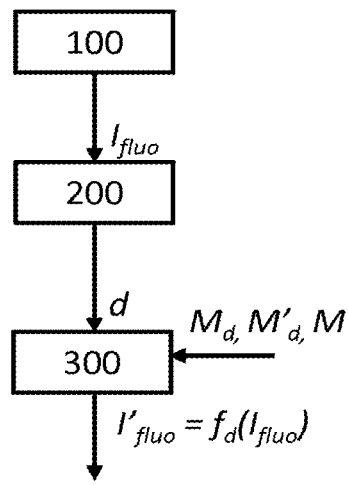

With reference to FIG. 7A, the main steps of a method for correcting a fluorescence image depending on the distance d between the excitation light source 11 and the object 10, according to this first embodiment, will now be described.

In a step 100, a fluorescence image $I_{fluo}$ is acquired. In a step 200, the distance d between the excitation light source 11 and the object 10 is measured, for example by means of the rangefinder 20 or by means of an automatic focusing system, i.e. an autofocus 27, which is described below.

The step 300 consists in applying a distance-correcting function $f_d$, dependent on said distance d, to each fluorescence image $I_{fluo}$, so as to obtain a corrected fluorescence image $I'_{fluo}$, according to equation (1a), (1b) or (1c).

In a second embodiment, the effect of the correction function is to compensate for variations in the intensity of the illuminance as a function of the distance between the object 10 and the light source 11.

Since the light source 11 is generally placed at a distance larger than 10 cm from the observed object, it may be considered, seen from the object, to be point-like. Under this assumption, the amount of light illuminating the object per unit area and time, i.e. the illuminance $\phi$, varies inversely proportional to the square of the distance d between the light source 11 and the object 10, according to what is called an inverse square law of the type $$\frac{1}{4\pi d^2}.$$

Now, the amount of fluorescence signal emitted by a fluorescent zone 13 of the object is proportional to the amount of excitation light reaching this zone per unit time, i.e. to the illuminance produced by the excitation light source of said zone. When the practitioner increases or decreases the distance between the probe 1 and a given fluorescent zone 13, the intensity of the fluorescence radiation emitted by this zone varies, and the magnitude of the signal $S_{fluo}$ of the region of interest $\Omega$ appearing in the fluorescence image is modified accordingly. The variation in brightness is thus very marked, because of the inverse square dependence on distance. For example, if the distance d increases from 20 cm to 40 cm, the brightness variation in the fluorescence image may reach a factor of 4.

If $\phi$ and $\phi_{ref}$ correspond to the illuminance produced by the excitation light source 11 at a distance d and at reference distance $d_{ref}$, respectively, then:

$$\frac{\phi}{\phi_{ref}} = \frac{d_{ref}^2}{d^2} \qquad (2)$$

Thus, if $I_{fluo-ref}(r)$ and $I_{fluo}(r)$ are the intensity of the fluorescence radiation originating from a given surface element $\delta S(r)$ and collected by a pixel of coordinate r of the image $I_{fluo}$ when the light source 11 is placed at the reference distance $d_{ref}$ and at the distance d from the object, respectively, then:

$$I_{fluro}(r) = I_{fluo-ref}(r) \times \frac{d_{ref}^2}{d^2}. \qquad (3)$$

In this embodiment, the effect of the correction function $f_d$ is to compensate for variation in distance with respect to the reference distance $d_{ref}$. Thus, if an image $I_{fluo}$ is acquired at a fluorescence distance d, the effect of the correction function is to divide the brightness $I_{fluo}(r)$ of each pixel, corresponding to a fluorescence zone 13, by a reference value $I_{fluo-ref}(r)$ corresponding to the reference distance $d_{ref}$. After correction, the corrected brightness $I'_{fluo}(r)$ of the pixel r is then:

$$I'_{fluo}(r) = f_d(I_{fluo}(r)) = I_{fluo}(r) \times \frac{d^2}{d_{ref}^2}. \qquad (4)$$

On account of equation (3), this becomes:

$$I'_{fluo}(r) \approx I_{fluo-ref}(r) \qquad (5),$$

the symbol $\approx$ representing an equality to within statistical fluctuations.

It is possible to apply this reasoning to all of the pixels making up a fluorescent image. Thus, if $I_{fluo}$ and $I'_{fluo}$ represent a fluorescence image before and after application of the correction function $f_d$, respectively, then:

$$I'_{fluo} = f_d(I_{fluo}) = I_{fluo} \times \frac{d^2}{d_{ref}^2}. \qquad (6a)$$

Each pixel of the image $I_{fluo}$ is then multiplied by the scalar $$\frac{d^2}{d_{ref}^2}.$$

The reference distance $d_{ref}$ may be a preset distance, for example 20 cm.

The reference distance $d_{ref}$ may also be determined, case by case, by the practitioner using the probe 1. The practitioner then has at his disposal a selector 15, for example a pushbutton, located on the probe 1, that is such that by actuating said selector 15 the distance at which the probe is located with respect to the object is considered to be a reference distance. This distance is then stored in a memory 32 as the reference distance for subsequent corrections to be made. This allows the reference distance $d_{ref}$ to be selected, case by case, depending on the fluorescence image ($I_{fluo}$) corresponding to this distance, this image being called the reference fluorescence image ($I_{fluo-ref}$). This selector 15 may be provided in all of the described embodiments.

Equation (5) shows that application of the correction function $f_d$ makes it so that a given fluorescent zone 13 produces, in the corrected fluorescence image $I'_{fluo}$, a region of interest $\Omega$, the brightness $I'_{fluo}(r)$ of each pixel of which is not very dependent, or even independent, of the distance d between the excitation light source 11 and the examined object 10.

According to one variant, the rangefinder 20 is an optical rangefinder and implements a pixelated photodetector allowing a measurement of a plurality of distances d(r') between the excitation source and a plurality of surface elements $\delta S(r')$ of the object (10), respectively. In other words, the rangefinding sensor 20 includes a matrix-array photodetector that detects the wave 22' reflected by the object. Each pixel of this photodetector is able to take a measurement of the distance separating it from the surface element of the object with which it is optically coupled, i.e. the surface element conjugated with this pixel. Such a photodetector may for example be a 3-D time-of-flight video camera, for example the model SR4000 sold by Mesa Imaging.

In this embodiment, it is possible to associate, with each pixel r of the fluorescence image $I_{fluo}$, a distance d(r') between the excitation source 11 and the surface element δS(r') conjugated with the pixel r.

The correction may therefore be made not by applying a scalar correction term to the entire image $I_{fluo}$, but, just as in the first embodiment, term by term, such that:

$$I'_{fluo}(r) = f_d(I_{fluo}(r)) = I_{fluo}(r) \times \frac{d(r')^2}{d_{ref}^2}. \quad (6b)$$

Another way of expressing this correction is to form, on the basis of each measured distance d(r'), a distance image D, each term D(r) of this distance image corresponding to the distance between the surface element δS(r') conjugated with the pixel r of the image $I_{fluo}$ and the excitation light source. The correction then comprises a term-by-term product of the fluorescence image $I_{fluo}$ multiplied by the square of the image D, weighted by the scalar $$\frac{1}{d_{ref}^2}.$$

This may be expressed as follows:

$$I'_{fluo}(r) = f_d(I_{fluo}(r)) = I_{fluo}(r) \times \frac{D(r)^2}{d_{ref}^2}. \quad (6c)$$

Figure 7B:
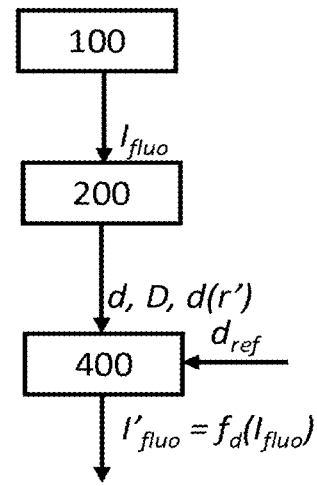

With reference to FIG. 7B, the main steps of a method for correcting a fluorescence image depending on the distance d between the excitation light source 11 and the object 10 according to this second embodiment will now be described. Steps 100 and 200 are similar to the same steps described with reference to FIG. 7A. The step 400 consists in applying a distance-correcting function $f_d$ that is dependent on said distance d to each fluorescence image $I_{fluo}$, so as to obtain a corrected fluorescence image according to equation (6a), (6b) or (6c).

The correction functions described in the first and second embodiments may be implemented independently of each other, but may also be combined.

Thus, in a third embodiment, the correction function combines the correction of the spatial nonuniformity of the illuminance and the compensation for distance. A correction function combining the correction functions described with reference to the first or second embodiment is applied to the image. This function $f_d$ may be such that:

$$I'_{fluo} = f_d(I_{fluo}) = \frac{I_{fluo}}{M'_d} \times \frac{d^2}{d_{ref}^2}, \text{ or} \quad (7a)$$

$$I'_{fluo} = f_d(I_{fluo}) = \frac{I_{fluo}}{M'_d} \times \frac{d(r')^2}{d_{ref}^2} \text{ or even} \quad (7b)$$

$$I'_{fluo} = f_d(I_{fluo}) = \frac{I_{fluo}}{M'_d} \times \frac{D(r)^2}{d_{ref}^2}. \quad (7c)$$

$M'_d$ here is the normalized illuminance image, such as described in one variant of the first embodiment.

Figure 7C:
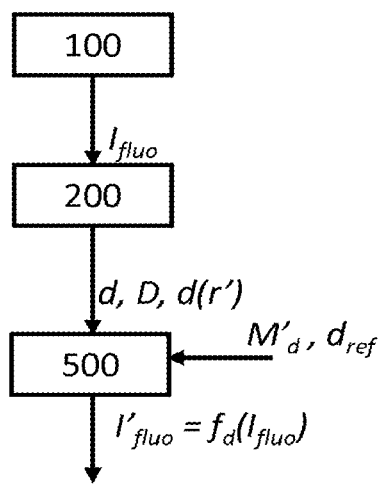

With reference to FIG. 7C, the main steps of a method for correcting a fluorescence image depending on the distance d between the excitation light source 11 and the object 10 according to this second embodiment will now be described. Steps 100 and 200 are similar to the same steps described with reference to FIG. 7A. The step 500 consists in applying a distance-correcting function $f_d$ that is dependent on said distance d to each fluorescence image $I_{fluo}$, so as to obtain a corrected fluorescence image $I'_{fluo}$ according to equation (7a), (7b) or (7c).

Other known correction functions may also be taken into account, in particular a correction function relative to exposure time, acting on each image so as to generate images normalized depending on a reference exposure time $t_{ref}$ defined beforehand, for example 50 ms.

Thus, in a fourth embodiment, the correction function $f_d$ may include a normalization term, taking the form of a ratio between the exposure time t of the fluorescence image and the reference exposure time $t_{ref}$. For example, in this embodiment, the correction function $f_d$ may be such that:

$$I'_{fluo} = f_d(I_{fluo}) = \frac{I_{fluo}}{M'_d} \times \frac{d^2}{d_{ref}^2} \times \frac{t_{ref}}{t} \text{ or:} \quad (8a)$$

$$I'_{fluo} = f_d(I_{fluo}) = \frac{I_{fluo}}{M_d} \times \frac{t_{ref}}{t} \text{ or:} \quad (8b)$$

$$I'_{fluo} = f_d(I_{fluo}) = \frac{I_{fluo}}{M'_d} \times \frac{d^2}{d_{ref}^2} \times \frac{t_{ref}}{t}. \quad (8c)$$

It will be noted that equations (8a) and (8c) use the normalized illuminance image $M'_d$ whereas equation (8c) uses the non-normalized illuminance image $M_d$.

Naturally, when the distance measurement is spatially resolved, i.e. when it is possible to determine a distance d(r') between each surface element δS(r') conjugated with a pixel r of the fluorescence image, then:

$$I'_{fluo} = f_d(I_{fluo}) = \frac{I_{fluo}}{M'_d} \times \frac{d(r')^2}{d_{ref}^2} \times \frac{t_{ref}}{t} \text{ or:} \quad (8d)$$

$$I'_{fluo} = f_d(I_{fluo}) = \frac{I_{fluo}}{M'_d} \times \frac{d(r')^2}{d_{ref}^2} \times \frac{t_{ref}}{t} \text{ or even} \quad (8e)$$

$$I'_{fluo} = f_d(I_{fluo}) = \frac{I_{fluo}}{M'_d} \times \frac{D(r)^2}{d_{ref}^2} \times \frac{t_{ref}}{t}. \quad (8f)$$

It will be noted that equations (8a), (8c), (8d), (8e) and (8f) use the normalized illuminance image $M'_d$ whereas equation (8b) uses the non-normalized illuminance image $M_d$.

Figure 7D:
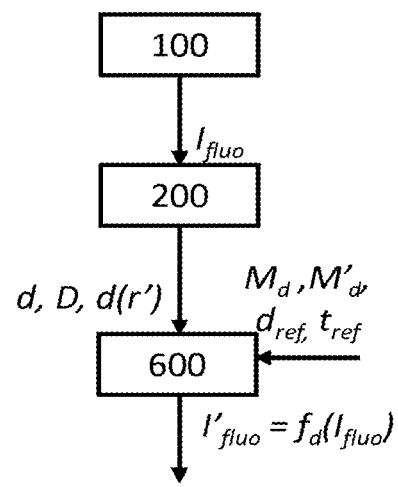

With reference to FIG. 7D, the main steps of a method for correcting a fluorescence image depending on the distance d between the excitation light source 11 and the object 10 according to this second embodiment will now be described. Steps 100 and 200 are similar to the same steps described with reference to FIG. 7A. The step 600 consists in applying a distance-correcting function $f_d$ that is dependent on said distance d to each fluorescence image $I_{fluo}$, so as to obtain a corrected fluorescence image according to one of equations (8a) to (8f).

Figure 8A:
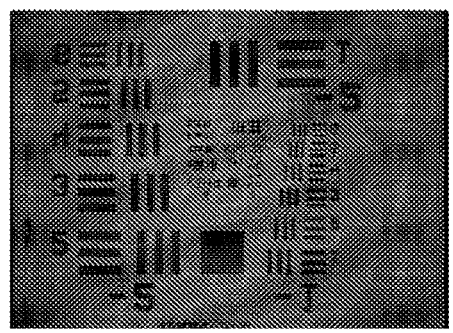

FIGS. 8A to 8D illustrate the effect of the correction functions described above on an image. FIG. 8A was obtained by placing the probe 1 shown in FIG. 2 facing a test card including dark patterns formed on a fluorescent screen such as described above. The test card was illuminated with an excitation beam, in an excitation spectral band centered on the wavelength of 750 nm, and the fluorescence image was formed by collecting fluorescence light in a fluorescence spectral band lying between 800 nm and 850 nm. The probe was placed at a distance d of 18 cm;

the exposure time t was 40 ms.

Figure 8B:
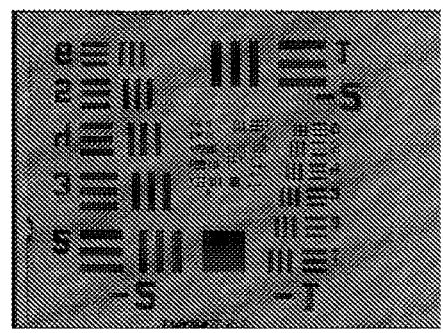

FIG. 8B shows an image formed using a correction function such as described in the first embodiment, by dividing, term by term, the fluorescence image $I_{fluo}$ by a normalized illuminance image $M'_d$ corresponding to the distance d=18 cm. It may be seen that, outside of the patterns of the test card, the grayscales of the obtained image are much more uniform. In particular, the borders of the image are not darker, unlike in the image 8A.

Figure 8C:
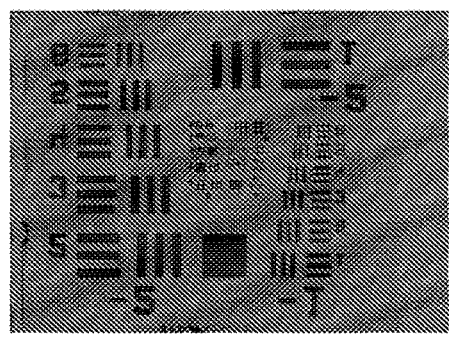

FIG. 8C shows an image formed using a correction function such as described in the third embodiment, combining the correction of illuminance and the compensation for distance, the reference distance $d_{ref}$ being equal to 20 cm. Slight darkening of the image is observed, because of the multiplication of each pixel by the scalar $$\frac{18^2}{20^2} \approx 0.8.$$

Figure 8D:
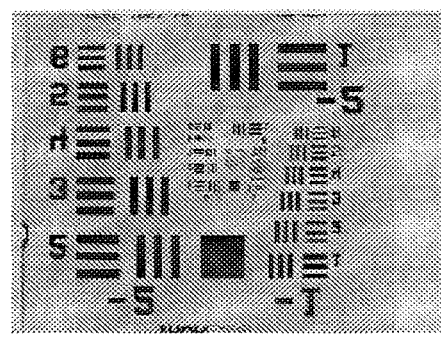

FIG. 8D shows an image formed using a correction function such as described in the fourth embodiment, combining the correction of the illuminance, the compensation of the distance with respect to a reference distance of 20 cm, and the normalization of exposure time, the reference exposure time $t_{ref}$ being 83 ms. Comparison of the images 8C and 8D allows the effect of the normalization by exposure time to be seen, the level of the grayscale of the lightest pixels being significantly increased because of the multiplication of each pixel by the scalar $$\frac{83}{40} \approx 2.$$

FIG. 9 shows another embodiment, in which the excitation light source is integrated into the probe 1. In this embodiment, the distance between the excitation light source 11 and the object 10 is not measured using a rangefinder, but using an autofocus system 27 that is able to automatically focus the object 10 on the fluorescence-image sensor 16. This autofocus system 27 is conventional. It achieves a focus on the basis of a measurement of the contrast of the fluorescence image $I_{fluo}$ at various focal lengths. According to one variant, the autofocus system 27 is based on what is called a phase-detection method, also known to those skilled in the art. The autofocus system 27 is able to deliver an item of information on the distance d between the excitation light source 11, which is securely fastened to the probe 1, and the examined object. It then acts as a distance detector.

However, the inventors consider that it is preferable to provide an optical, acoustic or microwave rangefinder 20 such as mentioned above, because this allows a more precise measurement of distance to be obtained more rapidly. Specifically, the contrast of the fluorescence image is often not high enough to allow this distance to be measured with sufficient reliability using an autofocus system. In addition, automatic determination of focal length with an autofocus system may be slow, and incompatible with the real-time constraints that must be met during a surgical intervention.

FIG. 10 shows another embodiment, in which the probe 1 includes a splitter 25, for example a semi-silvered mirror, able to direct the fluorescence optical radiation 14 incident on the probe to the matrix-array photodetector 19 through the fluorescence filter 17 described above, in order to form a fluorescence image ($I_{fluo}$). The splitter 25 is also able to direct optical radiation 24 incident on the probe 1, in a visible spectral band $I_{visible}$, to a second matrix-array photodetector 29 that is able to form an image $I_{visible}$ in visible light of the examined object. The matrix-array photodetector 29, the splitter 25 and the objective 18 form a visible-image sensor 26. By visible spectral band, what is meant is a spectral band the wavelengths of which lie in the visible, for example a band between 400 nm and 700 nm.

The processor 30 may then superpose the fluorescence image $I_{fluo}$, generated by the fluorescence-image sensor 16, and the visible image of the object, $I_{visible}$, generated by the visible-image sensor 26. Preferably, the optical axes of the visible-image sensor 16 and the fluorescence-image sensor 26 are coincident, so as to facilitate such a superposition. In this example, the objective 18 is common to the visible-image sensor 26 and to the fluorescence-image sensor 16. In one variant, the visible-image sensor comprises an objective 28 that is specific thereto.

The visible-image sensor 26 may comprise an automatic focusing system or autofocus 27, the visible image $I_{visible}$ of the object then being used to automatically adjust the focus. The autofocus system 27 is able to deliver information on the distance d between the excitation light source, which is securely fastened to the probe 1, and the examined object. It then acts as a distance detector.

It will be noted that a visible-image sensor 26 that is able to form an image $I_{visible}$ of the object in visible light may be provided in all of the embodiments disclosed in this application.

FIG. 11 shows one embodiment in which the rangefinder 20 is an optical rangefinder. By way of a semi-silvered mirror 25', the rangefinder 20 is able to emit a light wave through the optical system 18 of the fluorescence sensor 16. The semi-silvered mirror 25' reflects the optical wave 22 emitted by the rangefinder 20, and the optical wave 22' reflected by the object. It transmits the fluorescence light 14 emitted by the object 10 to the fluorescence photodetector 19.

Preferably, the rangefinder is positioned such that the light wave that it generates is centered with respect to said optical system 18. It then propagates toward the object 10 along the optical axis Z of the fluorescence sensor 16. This allows a measurement of the distance between the probe 1 and the point of the object located at the center of the image acquired by the sensor 16 to be taken whatever the distance between the probe and the object. The zone of the object targeted by the rangefinder 20 and on the basis of which the distance d is determined is then precisely known.

FIG. 12 shows another embodiment, in which the excitation light source 11 and the rangefinder 20 are located in a module 2 that is independent of the probe 1. For example, in this embodiment, the module 2 is a surgical light into which the rangefinder and the excitation light source 11 are integrated. The surgical light then allows the object 10 to be illuminated not only in a broad visible spectral band, in the same way as a conventional surgical light, but also more specifically in the excitation spectral band $\lambda_{ex}$ of the fluorophores potentially present in the object. The integration of the excitation light source 11 into a surgical light generally allows a more uniform spatial illuminance distribution to be obtained. In this embodiment, it is preferable to implement a correction dependent on the square of distance, as described with reference to FIG. 7B, and optionally also a correction dependent on exposure time.

FIG. 13 shows another embodiment, in which the excitation light source 11 is integrated into a module 2 that is independent of the probe 1, whereas the rangefinder 20 is securely fastened to the probe 1. The position of the module 2 with respect to the probe 1, and in particular the distance $d_2$ between the excitation light source 11 and the rangefinder 20, and optionally the orientation of the module 2 with respect to the probe 1, are known. In this embodiment, the rangefinder 20 measures the distance $d_1$ separating it from the object 10, the processor 30 then being able to determine the distance d between the excitation light source 11 and the object 10 on the basis of the measurement of the distance $d_1$ and of knowledge of the distance $d_2$, and optionally the orientation, of the module 2 with respect to the probe 1. In this embodiment, it is preferable to implement a correction dependent on the square of distance, as described with reference to FIG. 7B, and optionally also a correction dependent on exposure time.

In the embodiments described in FIGS. 1, 2, 11, 12 and 13, the rangefinder 20 may be a spatially resolved rangefinder, allowing a plurality of distances d(r') respectively between the excitation source and a plurality of surface elements δS(r') of the object (10) to be obtained, as described above.

The probe 1 such as described above may be implemented in open-surgery type applications, thereby allowing a surgical site to be observed. When the probe incorporates the excitation light source 11, as is shown in FIGS. 1, 8 and 9, it may also be used in other ways, in particular in endoscopy or in laparoscopy, provided its dimensions are suitably modified.

As specified in the first paragraphs of the detailed description, although the described embodiments relate to fluorescence imaging, which is the main application targeted in the short term, the described principles may be generalized to any type of image $I_{em}$ emitted by the object, whatever the emission spectral band, and in particular an image of radiation reflected by the object or an image of radiation backscattered by the object, the emission spectral band then corresponding to all or some of the excitation spectral band.

The invention claimed is:

1. A method for correcting a fluorescence image, comprising:
    illuminating an object using an excitation light source;
    detecting fluorescence radiation with a fluorescence-image sensor, the fluorescence radiation being emitted by the object under effect of the illumination;
    acquiring the fluorescence image with the fluorescence-image sensor based on the detected fluorescence radiation;
    measuring a distance between the excitation light source and the object;
    during a calibration phase, obtaining a plurality of illuminance images at respective different distances from the excitation light source, the illuminance images each being representative of a spatial distribution at a respective one of the distances, and storing the illuminance images in a memory;
    selecting one of the illuminance images, stored in the memory, corresponding to the measured distance; and
    applying an illuminance correction function to the fluorescence image using the selected illuminance image
    wherein in the illuminance correction function, two illuminance images respectively associated with two different measured distances are different from each other.

2. The correcting method as claimed in claim 1, the correction function comprising a term-by-term ratio of the fluorescence image to the illuminance image.

3. The correcting method as claimed in claim 1, wherein the fluorescence image is acquired in an exposure time, the correction function can normalize the fluorescence image with respect to a reference exposure time.

4. The correcting method as claimed in claim 1, wherein the correction function corrects the fluorescence image depending on the square of the measured distance.

5. The correcting method as claimed in claim 4, wherein the correction function takes into account the square of the measured distance and the square of a reference distance.

6. The correcting method as claimed in claim 5, further comprising selecting the reference distance depending on the fluorescence image.

7. The correcting method as claimed in claim 5, wherein the correction function applies a product of the fluorescence image multiplied by a ratio $$\left(\frac{d^2}{d_{ref}^2}\right)$$

between the square of the measured distance d and the square of the reference distance $d_{ref}$.

8. The correcting method as claimed in claim 1, wherein the distance between the excitation light source and the object is measured by a rangefinder configured to emit a wave in a direction of the object and to detect a wave reflected by the object, depending on which wave the distance is measured.

9. The correcting method as claimed in claim 8, wherein the rangefinder is a laser rangefinder or an ultrasonic rangefinder or a microwave rangefinder.

10. The correcting method as claimed in claim 1, wherein the distance between the excitation light source and the object is measured by an autofocus system that is configured to automatically establish a focus distance of the fluorescence-image sensor with respect to the object.

11. The correcting method as claimed in claim 10, further comprising acquiring a visible image of the object using a visible-image sensor.

12. A device for acquiring a fluorescence image, comprising:
    an excitation light source configured to illuminate an object in an excitation spectral band;
    a fluorescence-image sensor configured to collect fluorescence radiation emitted by the object, in a fluorescence spectral band, under effect of the illumination by the excitation light source, the fluorescence-image sensor configured to acquire a fluorescence image based on the collected fluorescence radiation;
    a rangefinder to measure a distance between the excitation light source and the object, the rangefinder configured to emit a wave in a direction of the object and to detect an optical wave reflected by the object, depending on which wave the distance is measured; and a processor configured to implement the method for correcting the fluorescence image that is the subject of claim 1.

13. The device for acquiring a fluorescence image as claimed in claim 12, wherein the fluorescence-image sensor is centered on an optical axis, the rangefinder configured to emit an optical wave along the optical axis.

14. The device for acquiring a fluorescence image as claimed in claim 12, wherein the fluorescence sensor includes a focusing optical system, the rangefinder configured to emit an optical wave in the direction of the object, the wave being centered using the optical system.

15. The device for acquiring a fluorescence image as claimed in claim 12, further comprising a selector of a reference distance, to store the reference distance in a memory.

16. The device for acquiring a fluorescence image as claimed in claim 12, wherein the processor is configured to, when the measured distance is between two of the different distances, obtain the illuminance image used in the illuminance image correction function by interpolating between illuminance images at the two of the different distances.

17. The correcting method as claimed in claim 1, wherein, when the measured distance is between two of the different distances considered during the calibration phase, the method comprises obtaining the illuminance image used in the illuminance image correction function by interpolating between illuminance images at the two of the different distances.

18. The correcting method as claimed in claim 1, wherein the calibration phase comprises:

placing a screen at the different distances from the light source; and at each distance, illuminating the screen with the light source and forming an illuminance image, representing the distribution of the illuminance produced, by the excitation light source, on the screen.

19. The correcting method as claimed in claim 18, wherein the screen is a uniform screen or a uniform fluorescent screen.

* * * * *